(12) United States Patent
Cheung

(10) Patent No.: US 9,433,657 B2
(45) Date of Patent: Sep. 6, 2016

(54) HEALTHCARE FOOD WITH ANTI-DIABETIC EFFECT AND PREPARATION METHOD THEREOF

(71) Applicant: Rose Cheung, Beverly Hills, CA (US)

(72) Inventor: Rose Cheung, Beverly Hills, CA (US)

(73) Assignee: Rose Cheung, Beverly Hills, CA (US)

(*) Notice: Subject to any disclaimer, the term of this patent is extended or adjusted under 35 U.S.C. 154(b) by 72 days.

(21) Appl. No.: 14/456,868

(22) Filed: Aug. 11, 2014

(65) Prior Publication Data

US 2016/0038556 A1 Feb. 11, 2016
US 2016/0206677 A9 Jul. 21, 2016

Related U.S. Application Data

(60) Provisional application No. 61/864,890, filed on Aug. 12, 2013, provisional application No. 61/864,885, filed on Aug. 12, 2013.

(51) Int. Cl.

| | |
|---|---|
| *A61K 36/74* | (2006.01) |
| *A61K 36/8994* | (2006.01) |
| *A61K 35/12* | (2015.01) |
| *A61K 36/752* | (2006.01) |
| *A61K 47/36* | (2006.01) |
| *A61K 9/16* | (2006.01) |
| *A23L 1/29* | (2006.01) |

(52) U.S. Cl.
CPC ............ *A61K 36/74* (2013.01); *A23L 1/296* (2013.01); *A61K 9/1652* (2013.01); *A61K 9/1682* (2013.01); *A61K 35/12* (2013.01); *A61K 36/752* (2013.01); *A61K 36/8994* (2013.01); *A61K 47/36* (2013.01); *A23V 2002/00* (2013.01)

(58) Field of Classification Search
None
See application file for complete search history.

(56) References Cited

FOREIGN PATENT DOCUMENTS

| | | | |
|---|---|---|---|
| CN | 101095851 A | | 1/2008 |
| CN | 101116510 A | | 2/2008 |
| CN | 101406644 A | | 4/2009 |
| CN | 102669660 A | | 9/2012 |
| CN | 102715502 A | * | 10/2012 |

OTHER PUBLICATIONS

English translation of CN102669660A, 27 pages.
English translation of 102715502A, 42 pages.
English abstract of CN101095851A, 1 page.
English abstract of CN101406644A, 1 page.
English abstract of CN101116510A, 1 page.
Article (Chinese language) Xiao-Feng Zhang; Bao-Ping Ji; Bo Li, Hua-Qiang Yu, titled: Effects of Paederia Scadens Extracts on Blood Glucose and Blood Lipid, 4 pages. College of Food Science and Nutritional Engineering, China Agricultural University, Beijing 100083, China, (Jul. 23, 2007).

* cited by examiner

*Primary Examiner* — Qiuwen Mi

(57) ABSTRACT

A healthcare foodstuff having an anti-diabetic effect and effective for treating type 2 diabetes mellitus. The healthcare foodstuff comprises effective ingredients and adjuvant(s), including *Paederia scandens*, coicis semen, pork and citri reticulatae pericarpium. Also disclosed is method of manufacturing the healthcare foodstuff useful in the treatment of type 2 diabetes mellitus.

10 Claims, 2 Drawing Sheets

HEALTHCARE FOOD WITH ANTI-DIABETIC EFFECT AND PREPARATION METHOD THEREOF

CROSS REFERENCE TO RELATED APPLICATIONS

Figure 1:
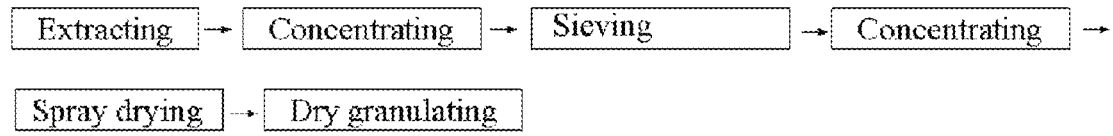

This application claims the benefit of the filing date of U.S. Provisional Patent Application No. 61/864,890, filed on Aug. 12, 2013, and the benefit of the filing date of U.S. Provisional Patent Application No. 61/864,885, filed on Aug. 12, 2013, the entire contents of which are incorporated herein by reference.

BACKGROUND OF THE DISCLOSURE

The present disclosure relates to a healthcare food or foodstuff (food and foodstuff are used interchangeably herein), particularly to a healthcare food or foodstuff having an anti-diabetic effect. More particularly, the present disclosure related to a healthcare food or foodstuff having anti-type 2 diabetes mellitus effect, and a method of preparing the healthcare food having an anti-diabetic effect thereof.

Type 2 diabetes mellitus (DM), also known as noninsulin-dependent diabetes mellitus (NIDDM) or adult-onset diabetes, is usually observed in people above 35-40 years old and accounts for more than 90% of all cases of DM. It is characterized by the inability of cells to respond adequately to normal levels of insulin produced by the body and resulting in failure in blood glucose control and relative insulin deficiency. Insulin secretion can be stimulated by certain oral medications. However, in the late stage of type 2 DM, some patients will still require insulin treatment similar to type 1 DM patients. This fundamentally means the short-term aim of type 2 DM treatment is to control the blood glucose levels, while the long-term aim is to prevent the occurrence and development of any complications related to DM. Although the basic treatment of type 2 DM consists of exercise and specific diet, medications and blood glucose monitoring are also very important. In the early stage of type 2 DM, the blood glucose level can usually be controlled by proper diet alone, increased physical activity and administration of sulfonylureas.

Patients with DM have a higher risk to develop heart disease, kidney disease and other health problems than healthy people. Furthermore, patients with type 2 DM are prone to hyperglycemic hyperosmolar nonketotic coma (NKHHC), common chronic microvascular complications including retinopathy, nephropathy, peripheral neuropathy and autonomic neuropathy, and macrovascular complications including, for example, atherosclerotic heart disease and peripheral vascular disease. Therefore, patients with Type 2 DM may need some medications for treatment or prevention of the complications.

In 2007, 39.81 million people in Mainland China (with Hong Kong, Macao, Taiwan excluded) (prevalence rate of 4.3%) suffered from diabetes, ranking second only to India, with 40.85 million people suffering from diabetes. It is estimated that by 2025, the total number of patients with DM will reach 59.27 million (prevalence rate of 5.6%). It should be noted that immune mediated destruction of pancreatic β-cells similar to that in Type 1 DM is also observed in some adult-onset diabetic patients. Patients with latent autoimmune diabetes of adults (LADA) do not require insulin treatment in the beginning stage and may be treated by using the same treatment for type 2 DM. Recently in China, notable progress has been observed in using traditional Chinese medicine solely for treatment of DM, such as Pien Tze Huang Jintangning Capsule. However, currently, there are no reports pertaining to the use of China Feverrine (*Paederia scandens*) as an ingredient in anti-diabetic healthcare traditional Chinese medicine.

*Paederia scandens* is an example of one kind of traditional Chinese medicine. *Paederia scandens* is the whole plant and the root of perennial herbaceous vine of *Paederia scandens* (LOUR.) MERRILL (Rubiaceae). After growing for 9-10 months, the aerial parts, except for those preserved as seeds, can be harvested annually in summer and autumn and sun-dried or cool-dried. Alternatively, the roots can be harvested in autumn, washed and sliced; and then dried in sunlight for medicinal use. It has a sweet and astringent flavour and is neutral in property. *Paederia scandens* is cultivated mainly in India, Indonesia, Malaysia, Japan, Korea, China and other Asian lands. In China, *Paederia scandens* can be found in the drainage basin of the Yangtze River and the southern areas thereof such as Shaanxi, Gansu, Shandong, Jiangsu, Anhui, Hubei, and Guizhou, among other areas.

*Paederia scandens* has shown efficacy in eliminating pathogenic wind, dampness and toxins, improving digestion and removing retention of food, relieving swelling, and promoting blood circulation to relieve pain. Further, it can promote blood circulation to relieve pain, clear away heat and toxins, invigorate spleen and resolve dampness.

SUMMARY OF THE DISCLOSURE

The instant disclosure provides a healthcare food or foodstuff having an anti-diabetic effect. More specifically, the healthcare foodstuff demonstrates efficacy in the treatment of type 2 diabetes. The healthcare food comprises effective ingredients and one or more adjuvants, in which the effective ingredients consist of *Paederia scandens*, coix seed (coicis semen), pork and dried tangerine peel (citri reticulatae pericarpium). The *Paederia scandens*, coicis semen, pork and citri reticulatae pericarpium are water (or aqueous) extracts from respective medical material thereof, and the adjuvant is water-soluble starch.

Citri reticulate pericarpium has been widely used as an herbal medicine for a long time in China, Korea, and Japan, and is known for its pharmacologic activity, rich resources, low toxicity, and costs. It is known that Citri reticulate pericarpium contains various bioactive compounds, such as flavonoids, phenolic acids, and limonoids, as well as volatile compounds which have strong pharmacologic bioactivities. (Evidence-Based Complementary and Alternative Medicine, Volume 2013 (2013))

In a preferred embodiment, the weight ratio of *Paederia scandens*, coicis semen, pork and citri reticulatae pericarpium in the effective ingredients is approximately 12:6:6:1.

The healthcare according to one embodiment of the instant disclosure can be prepared according to the following method:

Step 1: Extracting

The *Paederia scandens*, coicis semen, pork and citri reticulatae pericarpium are placed into a multi-functional extractor and then are decocted in water twice to obtain two decoctions.

Step 2: Concentrating

The two decoctions from step 1 are combined and filtered by a sieve of 120 Mesh. The filtrate is transferred into a vacuum concentrator and concentrated at 0.04-0.07 MPa at 60-80° C. Further feedings are performed intermittently depending on the evaporation rate. The initial feeding quantity is 5 cm below the level glass of the evaporating chamber;

Step 3: Sieving

The filtrate is concentrated until a plaster (relative density of 1.03-1.10, 60° C.) is obtained. The plaster is then filtered by a sieve with 120 Mesh to afford the healthcare food which is finally stored in a clean sealed container sterilized with 75% alcohol.

The extracting step of Step 1 discussed herein above comprises the following two steps:

(1) Adding water a first time in the amount of 7 times of the effective ingredients, soaking for 30 min and then decocting for 1 hour, and (2) Adding water a second time in the amount of 6 times of the effective ingredients, and decocting for 1 hour.

According to one aspect, the healthcare food of the instant disclosure can be formulated into tablets, capsules, oils, granules, dripping pills or oral solutions.

According to one aspect, granules comprised of the healthcare food of the instant disclosure can be prepared as follows:

Step 1—Spray Drying:

The plaster (discussed in the method of preparation herein above) is preheated to boil and then transferred into the feeder of the spray drying granulator. Soluble starch is placed into the fluidized bed of the spray drying granulator, lifted up and locked. The granulator is turned off and preheated to 100-105° C. to obtain dry powder. After 30 min, spray drying granulation is carried out according to known standard procedures of spray drying granulators.

Step 2—Dry Granulation:

After the pressure is stabilized, the dry powder is fed and strips are extruded. Once the strips are acceptable, normal production process is initiated. The dry strips are then crushed and passed through a sieve of 12 Mesh to afford granules containing 40-60% fine powder. The granules are then filtered further through No. 1 and No. 5 sieve respectively. The granules which can pass through the No. 1 sieve but cannot pass through the No. 5 sieve are deemed acceptable. For the granules and powder that are not acceptable, the dry granulation process in the dry press is repeated, and the obtained granules are sieved. The acceptable granules are then sealed in clean and dry plastic bags for further use.

The parameters for the spray drying process in the Step 1 of spray drying are as follows: inlet air temperature is approximately 115° C.-125° C.; outlet air temperature is approximately 90° C.-110° C., and minus pressure in the spray dryer is approximately −8 to −12 Pa. During the spray drying process, atomized state must be monitored at all time and the vibrator should be turned on to vibrate the spray drier periodically until the dry powders are obtained. The inlet air speed, outlet air speed and feeding rate in the Step 2 of spray granulation should be well controlled to afford granules with uniform size.

The instant disclosure also provides a method for preparing healthcare foods with anti-diabetic effect, said method comprising the following steps:

Step 1: Extracting

The *Paederia scandens*, coix seed (coicis semen), pork and dried tangerine peel (citri reticulatae pericarpium) are placed into a multi-functional extractor, and then are decocted in water for twice to obtain two decoctions.

Step 2: Concentrating

The decoctions from step 1 are combined and filtered through a sieve of 120 Mesh. The filtrate is transferred into a vacuum concentrator and concentrated at 0.04-0.07 MPa at 60-80° C. Further feedings are performed intermittently depending on the evaporation rate. The initial feeding quantity is 5 cm below the level glass of the evaporating chamber.

Step 3: Sieving

The filtrate is concentrated until a plaster (relative density of 1.03-1.10, 60° C.) is obtained. The plaster is then filtered through a sieve with 120 Mesh to afford the healthcare food which is finally stored in a clean sealed container sterilized with 75% alcohol.

The extracting step (Step 1) discussed herein above comprises the following two steps:

(1) Adding water a first time in the amount of 7 times of the effective ingredients, soaking for 30 min and then decocting for 1 hour.

(2) Adding water a second time in the amount of 6 times of the effective ingredients, and decocting for 1 hour.

In Step 1, each of the *Paederia scandens*, coicis semen, pork and citri reticulatae pericarpium is the water (aqueous) extract from respective medical material, and the weight ratio of *Paederia scandens*, coicis semen, pork and citri reticulatae pericarpium is approximately 12:6:6:1.

The healthcare food can be formulated into tablets, capsules, oils, granules, dripping pills or oral solutions.

Granules can be prepared by the following method:

Step 1 (Spray Drying):

The plaster is preheated to boil and then transferred into the feeder of the spray drying granulator. Soluble starch (q.s.) is placed into the fluidized bed of the spray drying granulator, lifted up and locked. The granulator is turned off and preheated to 100-105° C. After 30 min, spray drying granulation is carried out according to known standard procedures of spray drying granulators to obtain dry powder.

Step 2 (Dry Granulation):

After the pressure is stable, the dry powder is fed and strips are extruded. Once the strips are acceptable upon checking, normal production process is initiated. The dry strips are crushed and passed through a sieve of 12 Mesh to afford granules containing 40-60% fine powder. The granules are further filtered through No. 1 and No. 5 sieve respectively. The granules which can pass through the No. 1 sieve but cannot pass through the No. 5 sieve are acceptable granules. For the granules and powder that are deemed not acceptable, the dry granulation process in the dry press is repeated, and the obtained granules are sieved. The acceptable granules are then sealed in clean and dry plastic bags for further use.

In the Step 1 (spray drying), the parameters for spray drying process are as follows: inlet air temperature is 115° C.-125° C., outlet air temperature is 90° C.-110° C. and minus pressure in spray dryer is −8 to −12 Pa. During the drying process, atomized state must be monitored at all time and the vibrator should be turned on to vibrate the spray drier periodically until the dry powders are obtained.

In the Step 2 (dry granulation), the inlet air speed, outlet air speed and feeding rate should be well controlled during the spray granulation to afford granules with uniform size.

In accordance with the instant disclosure, the healthcare food as described herein is effective in clearing away heat and nourishing Yin, strengthening the spleen and nourishing the kidney as well as benefitting Qi, thus it is suitable for treating diabetes which is characterized by its deficiency of Yin and dryness-heat and deficiency of the spleen-Qi and kidney-Qi. It also provides healthcare benefit for the blood glucose levels of people with diabetes.

BRIEF DESCRIPTIONS OF THE FIGURES

Figure 2:
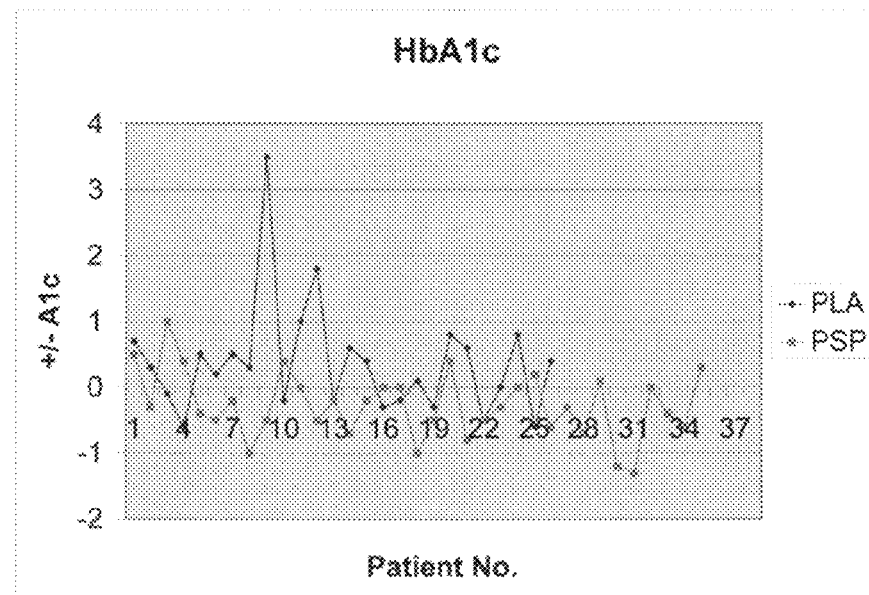

FIG. 1 illustrates the manufacturing procedure scheme for the preparation of granules FIG. 2 illustrates the effect of the healthcare food of the invention on reducing glycating haemoglobin (HbA1c).

Figure 3:
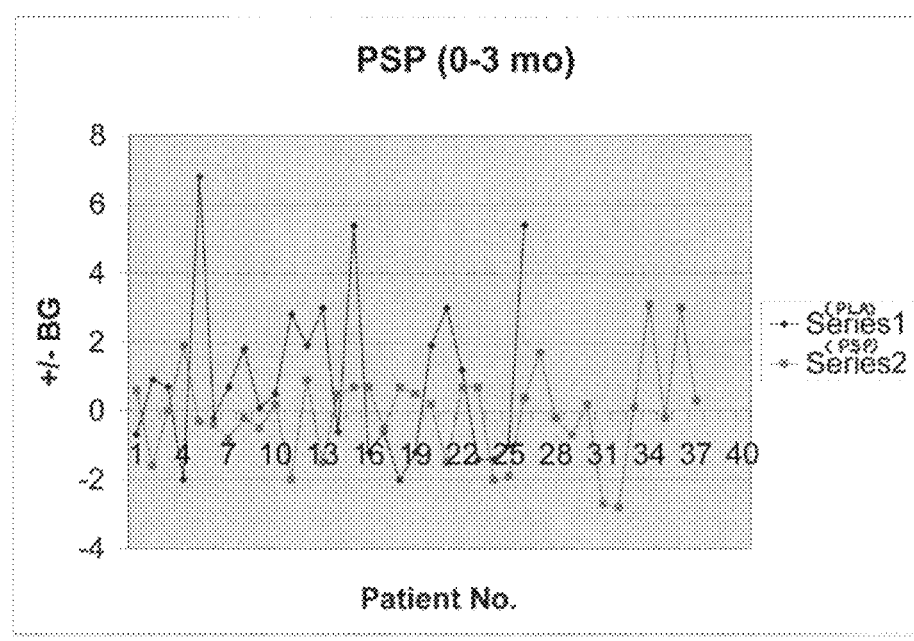

FIG. 3. illustrates the effect of the healthcare food of the invention on reducing blood glucose (BG).

DETAILED DESCRIPTION

The healthcare food of the present disclosure will be described below with reference to the figures and the examples.

The healthcare foodstuff according to the instant disclosure has been demonstrated to reduce glucose concentration in pre-diabetic subjects and lower glycating haemoglobin (HbA1c) level for both pre-diabetic and diabetic subjects. Further, the healthcare foodstuff of the instant disclosure will likely exert further beneficial effects, or demonstrate synergistic effects, to patients who have already received one or more Western medicines used for diabetic control.

The below examples describe the healthcare foodstuff according to the instant disclosure for use in treating patients suffering from diabetes, particularly type 2 diabetes mellitus (DM) and further set forth the methods for manufacturing granules comprising the healthcare foodstuff effective in treating DM. Additional experimental procedures and efficacy results are described and discussed.

EXAMPLES

The present disclosure is described in more detail with reference to the following examples, which are not intended to restrict the scope thereof.

Example 1

Method for Manufacturing Granules of Example 1

Effective ingredients according to the instant disclosure were weighed out as follows: *Paederia scandens* 102.16 kg; coicis semen 51.08 kg; pork 51.08 kg; and citri reticulatae pericarpium 8.68 kg.

Extracting

Step 1: *Paederia scandens*, coicis semen, pork and citri reticulatae pericarpium were placed into a multi-functional extractor and decocted in water twice to obtain two decoctions.

During the first decoction, water was added at an amount of 7 times of the effective ingredients, soaked for 30 min and then decocted for 1 hour.

During the second decoction, water was added at an amount of 6 times of the effective ingredients, and decocted for 1 hour.

Step 2: The two decoctions from step 1 were combined and filtered through a sieve of 120 Mesh. The filtrate was transferred into a vacuum concentrator and concentrated at 0.04 MPa at 60° C.; further feedings were performed intermittently depending on the evaporation rate; the initial feeding quantity was 5 cm below the level glass of the evaporating chamber.

Step 3: The filtrate was concentrated until a plaster (relative density of 1.03-1.10, 60° C.) was obtained. Then the plaster was filtered through a sieve with 120 Mesh to afford the healthcare food which was finally stored in a clean sealed container sterilized with 75% alcohol. The name of product, batch number, quantity, date, and location in refrigerator were noted for further use. The working region was cleared according to the clearing procedures (from extracting to concentrating) and the production record and the clearance record were completed in time.

Spray Drying Granulation

Step 1 (Spray Drying):

The plaster prepared in the extracting step was preheated to boil and then transferred into the feeder of the spray drying granulator. Soluble starch (q.$) was placed into the fluidized bed of the spray drying granulator, lifted up and locked. The granulator was turned off and was preheated to 100-105° C. to obtain dry powder. After 30 min, spray drying granulation was carried out according to known standard procedures of spray drying granulators.

For the spray drying process, the inlet air temperature was 115° C.; the outlet air temperature was 90° C. and the minus pressure in spray dryer was −8 Pa. During the spray drying process, atomized state must be monitored at all time and the vibrator should be turned on to vibrate the spray drier periodically until the dry powder was obtained.

Step 2 (Dry granulation):

After the pressure was stabilized, the dry powder was fed and strips were extruded. Once the strips were acceptable upon checking, normal production process was initiated. The dry strips were crushed and passed through a sieve of 12 Mesh to afford granules containing 40-60% fine powder. The granules were filtered further through No. 1 and No. 5 sieves respectively. The granules which could pass through the No. 1 sieve but could not pass through the No. 5 sieve were acceptable granules. For the granules and powder that were not acceptable, the dry granulation process in the dry press was repeated, and the obtained granules were sieved. The acceptable granules were then sealed in clean and dry plastic bags for further use.

The inlet air speed, outlet air speed and feeding rate should be well controlled during the spray granulation to afford granules with uniform size.

The resulting granules were sealed in clean plastic bags and placed into cap-sealed transfer barrels. The name of product, product specifications, batch number, quantity and date were noted, and the product was then placed in transfer room for test. After testing, if the resulting product was found to be acceptable, the packaging process was performed. The work area was cleared according to the clearing procedures (from extracting to concentrating) and the production record and the clearance record were completed in time.

Example 2

Effective ingredients according to the instant disclosure were weighed out as follows: *Paederia scandens* 60 kg; coicis semen 30 kg; pork 30 kg; and citri reticulatae pericarpium 5 kg.

Method for Manufacturing Granules of Example 2

Extracting

Step 1: The *Paederia scandens*, coicis semen, pork and citri reticulatae pericarpium were placed into a multi-functional extractor and then were decocted in water for twice to obtain two decoctions.

During the first decoction, water was added at an amount of 7 times of the effective ingredients, soaked for 30 min and then decocted for 1 hour.

During the second decoction, water was added at an amount of 6 times of the effective ingredients, and decocted for 1 hour.

Step 2: The two decoctions from step 1 were combined and filtered through a sieve of 120 Mesh. The filtrate was transferred into a vacuum concentrator and concentrated at 0.05 MPa at 70° C.; further feedings were performed intermittently depending on the evaporation rate; the initial feeding quantity was 5 cm below the level glass of the evaporating chamber.

Step 3: The filtrate was concentrated until a plaster (relative density of 1.03-1.10, 60° C.) was obtained. Then the plaster was filtered through a sieve with 120 Mesh to afford the healthcare food which was finally stored in a clean sealed container sterilized with 75% alcohol. The name of product, batch number, quantity, date, and location in refrigerator were noted for further use. The working region was cleared according to the clearing procedures (from extracting to concentrating) and the production record and the clearance record were completed in time.

Spray Drying Granulation

Step 1 (Spray Drying):

The plaster prepared in the extraction step was preheated to boil and then transferred into the feeder of the spray drying granulator. Soluble starch (q.s.) was placed into the fluidized bed of the spray drying granulator, lifted up and locked. The granulator was turned off and preheated to 100-105° C. to obtain dry powder. After 30 min, spray drying granulation was carried out according to known standard procedures of spray drying granulators.

For the spray drying process, the inlet air temperature was 120° C.; the outlet air temperature was 100° C. and the minus pressure in spray dryer was −10 Pa. During the spray drying process, atomized state must be monitored at all time and the vibrator should be turned on to vibrate the spray drier periodically until the dry powders were obtained.

Step 2 (Dry Granulation):

After the pressure was stable, the dry powder was fed and strips were extruded. Once the strips were acceptable upon checking, normal production process was initiated. The dry strips were crushed and passed through a sieve of 12 Mesh to afford granules containing 40-60% fine powder. The granules were filtered further through No. 1 and No. 5 sieve respectively. The granules which could pass through the No. 1 sieve but could not pass through the No. 5 sieve were acceptable granules. For the granules and powder that were not acceptable, the dry granulation process in the dry press was repeated, and the obtained granules were sieved. The acceptable granules were then sealed in clean and dry plastic bags for further use.

The inlet air speed, outlet air speed and feeding rate should be well controlled during the spray granulation to afford granules with uniform size.

The resulting granules were sealed in clean plastic bags and placed into cap-sealed transfer barrels. The name of product, product specifications, batch number, quantity and date were noted, and the product was placed in transfer room for test. After testing, if the resulting product was acceptable, the packaging process was performed. The work area was cleared according to the spray drying granulation procedures and the production record and the clearance record were completed in time.

Example 3

Effective ingredients were weighed out as follows: *Paederia scandens* 24 kg; coicis semen 12 kg; pork 12 kg and citri reticulatae pericarpium 2 kg.

Manufacturing Method of Granules of Example 3

Extracting

Step 1: The *Paederia scandens*, coicis semen, pork and citri reticulatae pericarpium were placed into a multi-functional extractor and then were decocted in water for twice to obtain two decoctions.

During the first decoction, water was added at an amount of 7 times of the effective ingredients, soaked for 30 min and then decocted for 1 hour.

During the second decoction, water was added at an amount of 6 times of the effective ingredients, and decocted for 1 hour.

Step 2: The two decoctions from step 1 were combined and filtered through a sieve of 120 Mesh. The filtrate was transferred into a vacuum concentrator and concentrated at 0.07 MPa at 80° C.; further feedings were performed intermittently depending on the evaporation rate; the initial feeding quantity was 5 cm below the level glass of the evaporating chamber.

Step 3: The filtrate was concentrated until a plaster (relative density of 1.03-1.10, 60° C.) was obtained. Then the plaster was filtered through a sieve with 120 Mesh to afford the healthcare food which was finally stored in a clean sealed container sterilized with 75% alcohol. The name of product, batch number, quantity and date were noted, and the product was placed in refrigerator for further use. The work area was cleared according to the clearing procedures (from extracting to concentrating) and the production record and the clearance record were completed in time.

Spray Drying Granulation

Step 1 (Spray Drying):

The plaster prepared in the extracting step was preheated to boil and then transferred into the feeder of the spray drying granulator. Soluble starch (q.$) was placed into the fluidized bed of the spray drying granulator, lifted up and locked. The granulator was turned off and preheated to 100-105° C. to obtain dry powder. After 30 min, spray drying granulation was carried out according to known standard procedures of spray drying granulators.

For the spray drying process, the inlet air temperature was 125° C.; the outlet air temperature was 110° C. and the minus pressure in spray dryer was −12 Pa. During the spray drying process, atomized state must be monitored at all time and the vibrator should be turned on to vibrate the spray drier periodically until the dry powders were obtained.

Step 2 (Dry Granulation):

After the pressure was stabilized, the dry powder was fed and strips were extruded. Once the strips were acceptable upon checking, normal production process was initiated. The dry strips were crushed and passed through a sieve of 12 Mesh to afford granules containing 40-60% fine powder. The granules were filtered further through No. 1 and No. 5 sieve respectively. The granules which could pass through the No. 1 sieve but could not pass through the No. 5 sieve were acceptable granules. For those that were not acceptable, the dry granulation process in the dry press was repeated, and the obtained granules were sieved. The acceptable granules were then sealed in clean and dry plastic bags for further use.

The inlet air speed, outlet air speed and feeding rate should be well controlled during the spray granulation to afford granules with uniform size.

The resulting granules were sealed in clean plastic bags and placed into cap-sealed transfer barrels. The name of product, product specifications, batch number, quantity and date were noted, and the product was placed in transfer room for test. After testing, if the resulting product was acceptable, the packaging process was performed. The work are was cleared according to the spray drying granulation procedure and the production record and the clearance record were completed in time.

Efficacy Test:

The following clinical research studies were performed to demonstrate the significant effect of the formula that comprises the healthcare foodstuff (PSP-1) on treating DM.

Report of First Phase Clinical Research Study of PSP-1

Subjects from Hong Kong and Macau were enrolled in the trial. Data from both groups were combined for analysis. After 3 months and 6 months of PSP-1 treatment (See Tables 1-4 and FIGS. 2 and 3), glycated haemoglobin (HbA1c) showed a significant decrease. The efficacy at 3 months is better than that at 6 months (p=0.008 and 0.020). Compared with the populations who were not treated by PSP-1 (baseline), the efficacy at 3 months showed that PSP-1 has positive effect on reducing the level of blood glucose and HbA1c.

PSP Test (Combined Data of Hong Kong and Macau)

TABLE 1

HbA1c (PSP-1 group) (by paired t test)

| HbA1c (PSP-1 group) | N | Mean | SD | P-value |
|---|---|---|---|---|
| 3 month after baseline | 27 | 7.015 | 1.0280 | 0.008* |
| | | 6.730 | 0.9659 | |
| 6 month after baseline | 25 | 7.028 | 1.0663 | 0.020* |
| | | 6.808 | 1.0324 | |

*P = 0.05

TABLE 2

HbA1c (Placebo group) (by paired t test)

| HbA1c (Placebo group) | N | Mean | SD | P-value |
|---|---|---|---|---|
| 3 month after baseline | 23 | 6.822 | 0.7495 | 0.057 |
| | | 7.196 | 1.0965 | |
| 6 month after baseline | 22 | 6.786 | 0.7472 | 0.096 |
| | | 7.341 | 1.5506 | |

TABLE 3

Fasting glucose (PSP-1 group) (by paired t test)

| Fasting glucose (PSP-1 group) | N | Mean | SD | P-value |
|---|---|---|---|---|
| 3 month after baseline | 28 | 7.554 | 1.6860 | 0.850 |
| | | 7.588 | 1.9436 | |
| 6 month after baseline | 26 | 7.588 | 1.7138 | 0.747 |
| | | 7.512 | 2.0498 | |

TABLE 4

Fasting glucose (Placebo group) (by paired t test)

| Fasting glucose (Placebo group) | N | Mean | SD | P-value |
|---|---|---|---|---|
| 3 month after baseline | 23 | 7.443 | 1.7681 | 0.067 |
| | | 8.626 | 2.8474 | |
| 6 month after baseline | 22 | 7.550 | 1.7325 | 0.233 |
| | | 8.768 | 4.5550 | |

Report of Second Phase Clinical Research Study of PSP-1

Inclusion Criteria

Diabetic Group (DG) Subjects
  A. with confirmed type 2 diabetes mellitus (DM), and
  B. blood glycosylated haemoglobin (HbA1c)>6.5%, or
  C. Fasting glucose >7.0 mmol/L, or
  D. 2 h glucose concentration in oral glucose tolerance test (OGTT)>11.1 mmol/L, and
  E. agreed not to accept other traditional Chinese medicine treatment during the trial period.

Pre-Diabetic Group (PG) Subjects
  A. Blood HbA1c ranged from 5.6% to 6.5%, or
  B. Fasting glucose=5.6 mmol/L to 6.9 mmol/L, or
  C. 2 h glucose concentration in OGTT=7.8 mmol/L to 11 mmol/L, and
  D. agreed not to accept other traditional Chinese medicine treatment during the trial period.

Exclusion Criteria:
  A. Patients with major problems associated with cardiac, respiratory, renal and hepatic functions;
  B. HIV subjects;
  C. Users of administering others prohibited substances;
  D. Use of any traditional Chinese medicine therapy for diabetes mellitus in at least one month prior to entering the study;
  E. Use of any other investigational drug(s) in at least one month prior to entering the study;
  F. Subjects who were considered by the investigator(s) unsuitable for the study or unable to comply with the treatment or the schedule of the trial in light of major illnesses.

Method
  A. Study Arrangement

All enrolled subjects were interviewed by a traditional Chinese medicine practitioner at the beginning of the study (baseline), the end of the 1st month and the end of 3rd month. Evaluation was performed at baseline and the end of the $3^{rd}$ month. Laboratory analysis was performed 3 times: at baseline, the end of the 1st month and the end of 3rd month.

B. Management of Administration of PSP-1

The subjects of DG and PG were administered 1 pack of PSP-1, bid, for 3 months.

C. Safety Monitoring of Biochemistry and Haematology Tests
    1. Alanine aminotransferase (ALT),
    2. Creatinine,
    3. Estimation of GFR (eGFR),
    4. Blood lipids,
    5. Complete blood picture (CBP),
  D. Test of Indicators for Assessing Efficacy of Treatment
    1. Fasting blood glucose,
    2. blood glycosylated hemoglobin (HbA1c),
    3. either standard oral glucose tolerance test (OGTT) or random glucose (2 h postprandial) was performed at baseline and at the end of the 3rd month,
    4. Urine samples were taken randomly at baseline, the end of the 1st month and the end of the 3rd month, and analyzed for urine albumin-to-creatinine ratio (UACR).

Test Results:

TABLE 5

Changes in biochemical indicators in PSP-1 combined group and placebo group

| | Group | | | | | |
|---|---|---|---|---|---|---|
| | DG + PG (n = 53) | | | Placebo group (n = 12) | | |
| Test | Baseline | 1 month after administrating PSP-1 | 3 month after administrating PSP-1 | Baseline | 1 month after administrating PSP-1 | 3 month after administrating PSP-1 |
| ALT | 44.3 ± 16.1 | 44.6 ± 17.2 | 43.1 ± 19.3 | 51.0 ± 43.9 | 55.33 ± 7.4 | 57.14 ± 6.3 |
| Creatinine | 75.8 ± 17.3 | 69.9 ± 17.3 | 73.2 ± 16.9 | 83.8 ± 15.5 | 72.2 ± 17.2 | 74.5 ± 13.8 |
| Total cholesterol | 5.1 ± 0.9 | 5.4 ± 1.2 | 5.4 ± 1.1 | 4.9 ± 0.8 | 4.8 ± 0.8 | 4.7 ± 0.8 |
| HDL-cholesterol | 1.4 ± 0.3 | 1.3 ± 0.4 | 1.3 ± 0.3 | 1.3 ± 0.3 | 1.3 ± 0.3 | 1.3 ± 0.3 |
| LDL-cholesterol | 3.1 ± 0.8 | 3.3 ± 1.0 | 3.3 ± 0.9 | 3.1 ± 0.7 | 3.0 ± 0.7 | 2.8 ± 0.6 |
| Triglyceride | 1.5 ± 0.9 | 1.7 ± 1.4 | 1.6 ± 0.9 | 1.1 ± 0.5 | 1.4 ± 0.5 | 1.2 ± 0.8 |
| Uric acid | 0.3 ± 0.1 | 0.3 ± 0.1 | 0.3 ± 0.1 | 0.4 ± 0.1 | 0.3 ± 0.0 | 0.3 ± 0.0 |
| Urea | 5.4 ± 1.4 | 5.4 ± 1.5 | 5.6 ± 1.6 | 5.5 ± 1.3 | 5.0 ± 1.1 | 6.0 ± 1.2 |
| UCAR | 0.02 ± 0.04 | 0.02 ± 0.02 | 0.02 ± 0.01 | 0.01 ± 0.00 | 0.02 ± 0.02 | 0.02 ± 0.04 |

As shown by the results in Table 5, no significant changes were observed for all biochemical indicators in both the combined group (DG+PG) and the placebo group. In addition, the EGFR levels of all subjects in PSP-1/placebo group were more than 60 mL/min/1.73 m$^2$ at baseline and 3 months after baseline and it is a normal level.

TABLE 6

Changes of fasting blood glucose concentration after 1 month and 3 months of administration of PSP-1/placebo in the DG, PG and placebo groups ("a" indicates P < 0.05)

| | | Test | | |
|---|---|---|---|---|
| | | Fasting blood glucose concentration (mmol/L) | | |
| Groups | | Baseline | 1 month after administrating PSP-1 | 3 months after administrating PSP-1 |
| DG | Diabetic (n = 34) | 8.3 ± 1.7 | 8.6 ± 1.6 | 8.1 ± 1.8 |
| | Placebo (n = 6) | 7.0 ± 0.9 | 7.9 ± 0.4 | 7.6 ± 1.9 |
| PG | Pre-diabetic (n = 19) | 6.1 ± 0.7$^a$ | 6.3 ± 0.8 | 5.9 ± 0.8$^a$ |
| | Placebo (n = 6) | 6.2 ± 0.5 | 6.4 ± 0.6 | 6.1 ± 0.6 |

Significant change in blood glucose concentration from 6.1 mmol/L to 5.9 mmol/L was observed in PG subjects treated with PSP-1 from baseline to 3 months after administrating PSP-1 (P<0.05). There was no such change in DG or placebo groups.

TABLE 7

Changes of HbA1c level in DG, PG and placebo groups at 1 month and 3 months after administrating PSP-1/placebo ("b" indicates P < 0.005; "c" indicates P = 0.001)

| | | Test | | |
|---|---|---|---|---|
| | | HbA1c (%) | | |
| Groups | | Baseline | 1 month after administrating PSP-1 | 3 months after administrating PSP-1 |
| DG | Diabetic (n = 34) | 7.2 ± 0.7b | 7.1 ± 0.7 | 6.9 ± 0.7$^b$ |
| | Placebo (n = 6) | 6.7 ± 0.4 | 6.6 ± 0.3 | 6.8 ± 0.5 |
| PG | Pre-diabetic (n = 19) | 6.2 ± 0.3$^c$ | 6.1 ± 0.3 | 6.0 ± 0.3$^c$ |
| | Placebo (n = 6) | 6.2 ± 0.4 | 6.2 ± 0.4 | 6.0 ± 0.5 |

For the DG subjects, significant decrease in HbA1c from 7.2% to 6.9% (P=0.003, i.e. P<0.005) was observed in subjects treated with PSP-1 from baseline to 3 months after administrating PSP-1. Such change was neither observed at 1 month after administrating PSP-1, nor in the placebo groups.

For the PG subjects, significant decrease in HbA1c from 6.2% to 6.0% (P=0.001) was observed in subjects treated with PSP-1 from baseline to 3 months after administrating PSP-1. Such change was neither observed at 1 month after administrating PSP-1, nor in the placebo groups.

TABLE 8

Changes of fasting blood glucose concentration and HbA1c level in the combined group treated with PSP-1 (DG + PG, n = 53) and the placebo group (n = 12) ("d" indicates P < 0.001)

| | Test | | | | | |
|---|---|---|---|---|---|---|
| | Fasting blood glucose (mmol/L) | | | HbA1c (%) | | |
| Group | Baseline | 1 month after administrating PSP-1 | 3 months after administrating PSP-1 | Baseline | 1 month after administrating PSP-1 | 3 months after administrating PSP-1 |
| DG + PG (n = 53) | 7.5 ± 1.7 | 7.7 ± 1.8 | 7.4 ± 1.8 | 6.8 ± 0.8$^d$ | 6.8 ± 0.8 | 6.6 ± 0.8$^d$ |
| Placebo (n = 12) | 6.5 ± 0.7 | 6.9 ± 0.9 | 6.6 ± 1.3 | 6.4 ± 0.5 | 6.3 ± 0.4 | 6.3 ± 0.6 |

There was no significant change in blood glucose concentration for all subjects. However, significant decrease in HbA1c from 6.8% to 6.6% in those treated with PSP-1 was observed from baseline to 3 months after administrating PSP-1 (P<0.001). No significant change was observed at 1 month after administrating PSP-1. Subjects in placebo groups showed no significant change in HbA1c.

Nineteen (19) DG subjects (16 treated with PSP-1 and 3 with placebo) and Twenty-two (22) PG subjects (16 treated with PSP-1 and 6 with placebo) undertook the oral glucose tolerance test (OGTT).

failure and determine the cause of acute kidney injury. It was performed on all subjects and all values were within the normal range. It demonstrated that PSP-1 did not cause any adverse effect on renal function and thus concluded that PSP-1 was safe to use.

As indicated from Table 6, PSP-1 showed better control for blood glucose concentration in the pre-diabetic group than in the diabetic group. There was a significant change in fasting blood glucose concentration in pre-diabetic subjects treated with PSP-1 (P<0.05) but no such change was observed for the diabetic group and the placebo group. It

TABLE 9

Changes of the glucose concentrations for DG (n = 19) and PG (n = 22) subjects in the OGTT

| | | Test | | | | | |
|---|---|---|---|---|---|---|---|
| | | Fasting glucose concentration (mmol/L) | | 1 hr glucose concentration (mmol/L) | | 2 hr glucose concentration (mmol/L) | |
| | Groups | Baseline | 3 months after administrating PSP-1 | Baseline | 3 months after administrating PSP-1 | Baseline | 3 months after administrating PSP-1 |
| DG | PSP-1 (n = 16) | 7.3 ± 1.2 | 7.1 ± 1.3 | 16.2 ± 3.3 | 15.0 ± 3.0 | 15.2 ± 4.9 | 15.04 ± 4.1 |
| | Placebo (n = 3) | 7.0 ± 1.5 | 7.6 ± 1.9 | 17.3 ± 3.1 | 17.7 ± 4.3 | 16.9 ± 8.3 | 17.0 ± 7.0 |
| PG | PSP-1 (n = 16) | 6.1 ± 0.6 | 5.8 ± 0.7 | 11.6 ± 3.4 | 11.0 ± 3.0 | 8.8 ± 2.7 | 8.8 ± 2.8 |
| | Placebo (n = 6) | 6.2 ± 0.8 | 6.1 ± 0.6 | 11.3 ± 3.6 | 11.5 ± 2.4 | 8.3 ± 2.8 | 8.8 ± 2.2 |

As seen in the data, there were no significant changes in fasting blood glucose concentrations, 1-hr post glucose intake and 2-hr post glucose intake conditions for all subjects after 3 months treatment with PSP-1. However, it was observed that there was a decreasing trend in blood glucose concentrations at baseline and 3 months after administrating PSP-1 for all subjects treated with PSP-1. No such trend was observed for the placebo subjects.

CONCLUSIONS

No reports on adverse effects were received for all subjects (DG, PG and placebo group) who completed the study. In addition, all biochemical tests (such as ALT, urea nitrogen and creatinine) and the haematological test (CBP) showed no significant changes for all subjects over the 3-month period of treatment (Table 5). Hence, the formula of PSP-1 has no harmful effect on the health of human body in view of clinic, biochemistry and haematology. The urea nitrogen-to-creatinine ratio was also used to predict renal might be due to the fact that the baseline fasting blood glucose concentration of the diabetic subjects had already stayed at high level and the 3-month period of treatment was not sufficient to reduce the blood glucose concentration significantly.

As shown in Table 7, PSP-1 had a lowering effect on HbA1c level in both DG and PG groups. For the DG group, the mean HbA1c level was reduced significantly from 7.2% at baseline to 6.9% after 3 months treatment with PSP-1 (P<0.005). For the PG group, the mean HbA1c was reduced significantly from 6.2% to 6.0% (P<0.001) which is below the upper limit of the normal level. For the combined group, a significant change in HbA1c was also observed. The mean HbA1c level was reduced from 6.8% at baseline to 6.6% after 3 months treatment with PSP-1. The results indicate that PSP-1 is effective in lowering HbA1c level, hence, it has a beneficial effect for the diabetic and pre-diabetic patients.

In general, 3 months supplementation of the PSP-1 formulation was able to reduce the blood glucose concentration in pre-diabetic subjects and lower HbA1c level for both pre-diabetic and diabetic subjects. Additional beneficial effects are likely be exerted on patients who have already received Western medicines for diabetic control.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A healthcare foodstuff having an anti-diabetic effect, wherein said healthcare foodstuff comprises effective ingredients and one or more adjuvants, in which the effective ingredients comprise *Paederia scandens*, coicis semen, pork and citri reticulatae pericarpium, and wherein the *Paederia scandens*, coicis semen, pork and citri reticulatae pericarpium are water extracts from respective medical material thereof, and the adjuvant is water-soluble starch.

2. The healthcare foodstuff according to claim 1, wherein the weight ratio of *Paederia scandens*, coicis semen, pork and citri reticulatae pericarpium in the effective ingredients is approximately 12:6:6:1.

3. The healthcare foodstuff according to claim 1, wherein the healthcare foodstuff is prepared by a method comprising the steps of:
   extracting the effective ingredients and decocting in water twice to obtain to decoctions;
   concentrating the two decoctions via filtration and vacuum concentration and evaporation; and
   sieving a filtrate that results from the concentrating step until a plaster is obtained.

4. The healthcare food with anti-diabetic effect of claim 3, wherein the decoction steps comprise:
   during the first decoction, adding water in an amount of 7 times of the effective ingredients, soaking 30 min and decocting for 1 hour; and
   during the second decoction, adding water in an amount of 6 times of the effective ingredients, and decocting for 1 hour.

5. The healthcare foodstuff according to claim 4, wherein the healthcare foodstuff can be formulated into tablets, capsules, oils, granules, dripping pills or oral solutions.

6. The healthcare foodstuff according to claim 5, wherein the healthcare foodstuff is used to treat type 2 diabetes mellitus.

7. The healthcare foodstuff according to claim 5, wherein the granules are prepared by a method comprising the steps of:
   spray dry granulation, wherein a plaster filtrate comprising the effective ingredients and a soluble starch are heated in a spray drying granulator to obtain dry powder, the dry powder undergoes spray dry granulation; and
   dry granulation, wherein the dry powder is stabilized to form extruded strips, the strips are crushed, sieved, filtered and dry granulated to form granules.

8. The healthcare foodstuff according to claim 7, wherein the parameters for the spray drying process in the spray drying step are: inlet air temperature is 115° C.-125° C.; outlet air temperature is 90° C.-110° C.; and minus pressure in spray dryer is −8 to −12 Pa.

9. The healthcare foodstuff according to claim 8, wherein an atomized state must be monitored at all times during the spray drying process, and the spray drier is vibrated periodically until dry powders are obtained.

10. The healthcare foodstuff according to claim 7, wherein the inlet air speed, outlet air speed and feeding rate in the spray granulation step should be well controlled to afford granules with uniform size.

\* \* \* \* \*